(12) United States Patent
Pasquier et al.

(10) Patent No.: US 7,056,349 B2
(45) Date of Patent: Jun. 6, 2006

(54) AGENT CONTAINING QUINONIMINE DERIVATIVES AND USED TO COLOR KERATIN FIBRES, AND ASSOCIATED METHOD

(75) Inventors: Cécile Pasquier, Marly (CH); Veronique Buclin-Charrière, Morlon (CH); Patrick Wyss, Neyruz (CH)

(73) Assignee: Wella AG, Darmstadt (DE)

( * ) Notice: Subject to any disclaimer, the term of this patent is extended or adjusted under 35 U.S.C. 154(b) by 418 days.

(21) Appl. No.: 10/344,873

(22) PCT Filed: Feb. 23, 2002

(86) PCT No.: PCT/EP02/01925

§ 371 (c)(1),
(2), (4) Date: Feb. 14, 2003

(87) PCT Pub. No.: WO02/102336

PCT Pub. Date: Dec. 27, 2002

(65) Prior Publication Data

US 2003/0182736 A1    Oct. 2, 2003

(30) Foreign Application Priority Data

Jun. 19, 2001    (DE) ................................ 101 29 545

(51) Int. Cl.
*A61K 7/13*    (2006.01)
(52) U.S. Cl. ...................... 8/405; 8/406; 8/410; 8/411; 8/421; 8/424; 8/455; 552/302
(58) Field of Classification Search .................... 8/405, 8/406, 411, 421, 424, 455, 410; 552/293, 552/302
See application file for complete search history.

(56) References Cited

U.S. PATENT DOCUMENTS 3,041,244 A    6/1962    Feit ............................. 167/88
3,963,764 A    6/1976    Kalopissis et al. .......... 760/396

FOREIGN PATENT DOCUMENTS

DE    1 203 042      10/1965
DE    1203042 B  *   10/1965
DE    199 32 565 A1    1/2001

OTHER PUBLICATIONS

R,K Norris et al., 2-substituted and 2,6-disubstituted 1,4-benzoquinone 4-oximes acetates, Australian Jornal of Chemistry, 24, 1971, pp. 1449-1465.*
George G. Guilbault et al. "Specific detection and determination of cyanide Using Various Quinone Derivatives"., Analen Der Chemie, 37, 1965, pp. 1395-1399.*
STIC Search Report.*
Nair V. et al: "Dipolar Cycloaddition of Carbonyl Ylides ... " Tetrahedron Letters, Elsevier Science Publishers, Amsterdam, NL, BD. 42, NR. 10, Mar. 4, 2001, pp. 2045-2046.
R.K. Norris et al: "2-Substituted and 2,6-Disubstituted ... ", Australian Journal of Chemistry, 24, 1971, pp. 1449-1465.
George G. Guilbault et al: "Specific Detection and Determination of Cyanide ... ", Analen Der Chemie, 37, 1965, pp. 1395-1399.
Tsutomu Ishikawa, et al "Nitrosation of Phenolic Substrates Under Mildly ... ", J. Org. Chem 1996, 61, pp. 2774-2779.
Tsutomu Ishikawa et al. "Synthesis of Macarpine and Its Cytotoxicity ... " Tetrahedron, vol. 51, No. 31, pp. 8447-8458, 1995.
Tsutomu Ishikawa et al "Experimental Section", J. Org. Chem., vol. 61, No. 8, 1996.

* cited by examiner

*Primary Examiner*—Eisa Elhilo
(74) *Attorney, Agent, or Firm*—Michael J. Striker

(57) ABSTRACT

The invention relates to an agent for colouring fibres (A). Said agent is produced by mixing two constituents (A1) and (A2), and is characterised in that the constituent (A1) contains at least one quinonimine derivative of formula (I), and the constituent (A2) contains at least one compound from the group consisting of aromatic amines and phenols. The invention also relates to a method for colouring keratin fibres using the inventive agent.

13 Claims, No Drawings

AGENT CONTAINING QUINONIMINE DERIVATIVES AND USED TO COLOR KERATIN FIBRES, AND ASSOCIATED METHOD

The object of the present invention is an agent for dyeing keratin fibers, for example silk, wool or hair, particularly human hair, which contains a combination of (i) at least one quinonimine derivative of formula (I) and (ii) at least one aromatic amine or phenol, as well as a method of dyeing keratin fibers by use of said dyeing agent.

Hair dyeing agents can be divided mainly into oxidative colorants and toners, depending on the starting compound doing the dyeing and the end result desired. Oxidation hair dyes are eminently suited for covering high proportions of gray hair, the oxidative colorants used to cover up a proportion of up to 50% of gray hair as a rule being referred to as oxidative toners, whereas the oxidative colorants used for gray hair areas exceeding 50% or for "color brightening" are as a rule referred to as oxidative dyes. Direct dyes are contained mainly in nonoxidative colorants (known as toning agents). Some direct dyes, for example the nitro dyes, because of their small molecular size, can penetrate into the hair and—at least in the outer regions—color it directly. Such toners are very gentle to the hair and as a rule withstand 6 to 8 hair washings. Direct dyes, particularly the nitro dyes, are also often used in oxidative colorants to create certain shades or to intensify the coloration.

The use of imines in hair colorants is known from the literature. For example, German Unexamined Patent Application DE 199 32 565 describes hair colorants containing n-haloimines. The compounds described in that document, however, do not meet the requirements placed on colorants for keratin fibers in every respect. Hence, a great demand continued to exist for gentle colorants which under mild conditions would provide intense colorations.

Surprisingly, we have now found that by use of a combination of (i) at least one quinonimine of formula (I) and (ii) at least one amine and/or phenol, intense colorations in a great variety of color shades can be obtained in a gentle manner and under mild conditions, even in the absence of oxidants. The combination according to the invention also provides cleaner colors than do common oxidative colorants.

Hence, the object of the present invention is an agent for dyeing fibers (A), for example wool, silk, cotton [sic-Translator] or hair, particularly human hair, which is prepared by mixing two components, (A1) and (A2), and is characterized in that component (A1) contains at least one quinonimine of formula (I) and component (A2) contains at least one compound from the group consisting of aromatic amines and phenols:

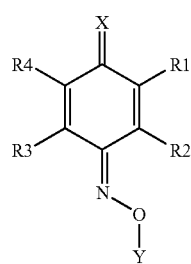

(I)

wherein in formula (I)
X denotes oxygen or an NR group (in which R stands for an optionally substituted $(C_1-C_6)$-alkyl group or an optionally substituted aromatic isocyclic or heterocyclic ring);
Y denotes a $(C_1-C_6)$-alkylsulfonyl group, arylsulfonyl group or acetyl group;
R1, R2, R3 and R4 can be equal or different and independently of each other denote hydrogen, a halogen atom (F, Cl, Br, I), a $(C_1-C_6)$-alkyl group, a trifluoromethyl group, a halogen (F, Cl, Br, I)-substituted $(C_1-C_6)$-alkyl group, a $(C_1-C_6)$-hydroxyalkyl group, a $(C_2-C_6)$-polyhydroxyalkyl group, a $(C_1-C_6)$-aminoalkyl group, a $(C_1-C_6)$-alkoxy group, a $(C_1-C_6)$-hydroxyalkoxy group, a $(C_1-C_6)$-aminoalkoxy group, a $(C_1-C_6)$-alkoxy-$(C_1-C_6)$-alkyl group, a $(C_1-C_6)$-alkoxy-$(C_1-C_6)$-alkoxy group, a $(C_1-C_8)$-hydroxyalkyl-$(C_1-C_6)$-aminoalkyl group, a nitro group, a cyano group, a carboxyl group, a carboxylate ester group or an optionally substituted aromatic (isocyclic or heterocyclic) ring system, with two adjacent R1 to R4 groups together possibly forming a condensed aromatic (isocyclic or heterocyclic) ring system.

Preferred are compounds of formula (I) wherein X denotes oxygen, Y denotes a methylsulfonyl group, a phenylsulfonyl group, a 4-tolylsulfonyl group, a 4-chlorophenylsulfonyl group, an acetyl group or a chloroacetyl group, and R1, R2, R3 and R4 can be equal or different and independently of each other denote hydrogen, a halogen atom (F, Cl, Br, I), a $(C_1-C_6)$-alkyl group, a $(C_1-C_6)$-hydroxyalkyl group, a $(C_1-C_6)$-aminoalkyl group, a $(C_1-C_6)$-alkoxy group, a $(C_1-C_6)$-hydroxyalkyl-$(C_1-C_6)$-aminoalkyl group, a $(C_1-C_6)$-alkoxy-$(C_1-C_6)$-alkyl group, a carboxyl group or an optionally substituted aromatic (isocyclic or heterocyclic) ring system with two adjacent R1 to R4 groups together possibly forming a condensed aromatic (isocyclic or heterocyclic) ring.

Suitable compounds of formula (I) are, for example:
1,4-benzoquinone-4-[O-(methylsulfonyl)oxime];
2-methyl-1,4-benzoquinone-4-[O-(methylsulfonyl)oxime];
2-chloro-1,4-benzoquinone-4-[O-(methylsulfonyl)oxime];
2-bromo-1,4-benzoquinone-4-[O-(methylsulfonyl)oxime];
2-fluoro-1,4-benzoquinone-4-[O-(methylsulfonyl)oxime];
2-hydroxymethyl-1,4-benzoquinone-4-[O-(methylsulfonyl)oxime];
2-hydroxyethyl-1,4-benzoquinone-4-[O-(methylsulfonyl)oxime];
2-aminomethyl-1,4-benzoquinone-4-[O-(methylsulfonyl)oxime];
2-methoxymethyl-1,4-benzoquinone-4-[O-(methylsulfonyl)oxime];
2-[(2-hydroxyethyl)amino]methyl-1,4-benzoquinone-4-[O-(methylsulfonyl)oxime];
2-hydroxycarbonyl-1,4-benzoquinone-4-[O-(methylsulfonyl)oxime];
3-methyl-1,4-benzoquinone-4-[O-(methylsulfonyl)oxime];
3-chloro-1,4-benzoquinone-4-[O-(methylsulfonyl)oxime];
3-bromo-1,4-benzoquinone-4-[O-(methylsulfonyl)oxime];
3-fluoro-1,4-benzoquinone-4-[O-(methylsulfonyl)oxime];

3-hydroxymethyl-1,4-benzoquinone-4-[O-(methylsulfonyl)oxime];
2,6-dichloro-1,4-benzoquinone-4-[O-(methylsulfonyl)oxime];
2,6-dibromo-1,4-benzoquinone-4-[O-(methylsulfonyl)oxime];
2,5-dimethyl-1,4-benzoquinone-4-[O-(methylsulfonyl)oxime];
2-isopropyl-5-methyl-1,4-benzoquinone-4-[O-(methylsulfonyl)oxime];
2-methyl-5-isopropyl-1,4-benzoquinone-4-[O-(methylsulfonyl)oxime];
1,4-naphthoquinone-4-[O-(methylsulfonyl)oxime];
1-phenyliminobenzoquinone-4-[O-(methylsulfonyl)oxime];
1-methyliminobenzoquinone-4-[O-(methylsulfonyl)oxime];
1,4-benzoquinone-4-[O-(phenylsulfonyl)oxime];
2-methyl-1,4-benzoquinone-4-[O-(phenylsulfonyl)oxime];
2-chloro-1,4-benzoquinone-4-[O-(phenylsulfonyl)oxime];
2-bromo-1,4-benzoquinone-4-[O-(phenylsulfonyl)oxime];
2-fluoro-1,4-benzoquinone-4-[O-(phenylsulfonyl)oxime];
2-hydroxymethyl-1,4-benzoquinone-4-[O-(phenylsulfonyl)oxime];
2-hydroxyethyl-1,4-benzoquinone-4-[O-(phenylsulfonyl)oxime];
2-aminomethyl-1,4-benzoquinone-4-[O-(phenylsulfonyl)oxime];
2-methoxymethyl-1,4-benzoquinone-4-[O-(phenylsulfonyl)oxime];
2-[(2-hydroxyethyl)amino]methyl-1,4-benzoquinone-4-[O-(phenylsulfonyl)oxime];
2-hydroxycarbonyl-1,4-benzoquinone-4-[O-(phenylsulfonyl)oxime];
3-methyl-1,4-benzoquinone-4-[O-(phenylsulfonyl)oxime];
3-chloro-1,4-benzoquinone-4-[O-(phenylsulfonyl)oxime];
3-bromo-1,4-benzoquinone-4-[O-(phenylsulfonyl)oxime];
3-fluoro-1,4-benzoquinone-4-[O-(phenylsulfonyl)oxime];
3-hydroxymethyl-1,4-benzoquinone-4-[O-(phenylsulfonyl)oxime];
2,6-dichloro-1,4-benzoquinone-4-[O-(phenylsulfonyl)oxime];
2,6-dibromo-1,4-benzoquinone-4-[O-(phenylsulfonyl)oxime];
1,4-benzoquinone-4-[O-4-(tolylsulfonyl)oxime];
2-methyl-1,4-benzoquinone-4-[O-4-(tolylsulfonyl)oxime];
2-chloro-1,4-benzoquinone-4-[O-4-(tolylsulfonyl)oxime];
2-bromo-1,4-benzoquinone-4-[O-4-(tolylsulfonyl)oxime];
2-fluoro-1,4-benzoquinone-4-[O-4-(tolylsulfonyl)oxime];
2-hydroxymethyl-1,4-benzoquinone-4-[O-4-(tolylsulfonyl)oxime];
2-hydroxyethyl-1,4-benzoquinone-4-[O-4-(tolylsulfonyl)oxime];
2-aminomethyl-1,4-benzoquinone-4-[O-4-(tolylsulfonyl)oxime];
2-methoxymethyl-1,4-benzoquinone-4-[O-4-(tolylsulfonyl)oxime];
2-[(2-hydroxyethyl)amino]methyl-1,4-benzoquinone-4-[O-4-(tolylsulfonyl)oxime];
2-hydroxycarbonyl-1,4-benzoquinone-4-[O-4-(tolylsulfonyl)oxime];
3-methyl-1,4-benzoquinone-4-[O-4-(tolylsulfonyl)oxime];
3-chloro-1,4-benzoquinone-4-[O-4-(tolylsulfonyl)oxime];
3-bromo-1,4-benzoquinone-4-[O-4-(tolylsulfonyl)oxime];
3-fluoro-1,4-benzoquinone-4-[O-4-(tolylsulfonyl)oxime];
3-hydroxymethyl-1,4-benzoquinone-4-[O-4-(tolylsulfonyl)oxime];
2,6-dichloro-1,4-benzoquinone-4-[O-4-(tolylsulfonyl)oxime];
2,6-dibromo-1,4-benzoquinone-4-[O-4-(tolylsulfonyl)oxime];
1,4-benzoquinone-4-(O-acetyloxime);
2-methyl-1,4-benzoquinone-4-(O-acetyloxime);
2-chloro-1,4-benzoquinone-4-(O-acetyloxime);
2-bromo-1,4-benzoquinone-4-(O-acetyloxime);
2-fluoro-1,4-benzoquinone-4-(O-acetyloxime);
2-hydroxymethyl-1,4-benzoquinone-4-(O-acetyloxime);
2-hydroxyethyl-1,4-benzoquinone-4-(O-acetyloxime);
2-aminomethyl-1,4-benzoquinone-4-(O-acetyloxime);
2-methoxymethyl-1,4-benzoquinone-4-(O-acetyloxime);
2-[(2-hydroxyethyl)amino]methyl-1,4-benzoquinone-4-(O-acetyloxime);
2-hydroxycarbonyl-1,4-benzoquinone-4-(O-acetyloxime);
3-methyl-1,4-benzoquinone-4-(O-acetyloxime);
3-chloro-1,4-benzoquinone-4-(O-acetyloxime);
3-bromo-1,4-benzoquinone-4-(O-acetyloxime);
3-fluoro-1,4-benzoquinone-4-(O-acetyloxime);
3-hydroxymethyl-1,4-benzoquinone-4-(O-acetyloxime);
2,6-dichloro-1,4-benzoquinone-4-(O-acetyloxime) and
2,6-dibromo-1,4-benzoquinone-4-(O-acetyloxime).

The following among the aforesaid compounds of formula (I) are particularly preferred:
1,4-benzoquinone-4-[O-(methylsulfonyl)oxime];
2-methyl-1,4-benzoquinone-4-[O-(methylsulfonyl)oxime];
2-chloro-1,4-benzoquinone-4-[O-(methylsulfonyl)oxime];
2-bromo-1,4-benzoquinone-4-[O-(methylsulfonyl)oxime];
2-fluoro-1,4-benzoquinone-4-[O-(methylsulfonyl)oxime];
2-hydroxymethyl-1,4-benzoquinone-4-[O-(methylsulfonyl)oxime];
2-hydroxyethyl-1,4-benzoquinone-4-[O-(methylsulfonyl)oxime];
2-aminomethyl-1,4-benzoquinone-4-[O-(methylsulfonyl)oxime];
2-methoxymethyl-1,4-benzoquinone-4-[O-(methylsulfonyl)oxime];
2-[(2-hydroxyethyl)amino]methyl-1,4-benzoquinone-4-[O-(methylsulfonyl)oxime];
2-hydroxycarbonyl-1,4-benzoquinone-4-[O-(methylsulfonyl)oxime];
3-methyl-1,4-benzoquinone-4-[O-(methylsulfonyl)oxime];
3-chloro-1,4-benzoquinone-4-[O-(methylsulfonyl)oxime];

3-bromo-1,4-benzoquinone-4-[O-(methylsulfonyl)oxime];
3-fluoro-1,4-benzoquinone-4-[O-(methylsulfonyl)oxime];
3-hydroxymethyl-1,4-benzoquinone-4-[O-(methylsulfonyl)oxime];
2,6-dichloro-1,4-benzoquinone-4-[O-(methylsulfonyl)oxime];
2,6-dibromo-1,4-benzoquinone-4-[O-(methylsulfonyl)oxime];
2,5-dimethyl-1,4-benzoquinone-4-[O-(methylsulfonyl)oxime];
2-isopropyl-5-methyl-1,4-benzoquinone-4-[O-(methylsulfonyl)oxime];
2-methyl-5-isopropyl-1,4-benzoquinone-4-[O-(methylsulfonyl)oxime] and
1,4-naphthoquinone-4-[O-(methylsulfonyl)oxime];

Suitable aromatic amines are aromatic (isocyclic or heterocyclic) compounds with at least one amino group, and suitable phenols are aromatic (isocyclic or heterocyclic) compounds with at least one hydroxyl group.

Examples of amines and phenols contained in component (A2) are in particular: N-(3-dimethylaminophenyl)urea; 2,6-diaminopyridine; 2-amino-4-[(2-hydroxyethyl)-amino]anisole; 2,4-diamino-1-fluoro-5-methylbenzene; 2,4-diamino-1-methoxy-5-methylbenzene; 2,4-diamino-1-ethoxy-5-methylbenzene; 2,4-diamino-1-(2-hydroxy-ethoxy)-5-methylbenzene; 2,4-di[(2-hydroxyethyl)amino]-1,5-dimethoxybenzene; 2,3-diamino-6-methoxypyridine; 3-amino-6-methoxy-2-(methylamino)pyridine; 2,6-diamino-3,5-dimethoxypyridine; 3,5-diamino-2,6-dimethoxypyridine; 1,3-diaminobenzene; 2,4-diamino-1-(2-hydroxyethoxy)benzene; 1,3-diamino-4-(2,3-dihydroxypropoxy)benzene; 1,3-diamino-4-(3-hydroxypropoxy)benzene; 1,3-diamino-4-(2-methoxyethoxy)benzene; 2,4-diamino-1,5-di(2-hydroxyethoxy)benzene; 1-(2-aminoethoxy)-2,4-diaminobenzene; 2-amino-1-(2-hydroxyethoxy)-4-methylaminobenzene; 2,4-diaminophenoxyacetic acid; 3-[di(2-hydroxyethyl)amino]aniline; 4-amino-2-di[(2-hydroxyethyl)amino]-1-ethoxybenzene; phenol; 5-methyl-2-(1-methylethyl)phenol; 3-[(2-hydroxyethyl)amino]aniline; 3-[(2-aminoethyl)amino]aniline; 1,3-di(2,4-diaminophenoxy)propane; di(2,4-diaminophenoxy)methane; 1,3-diamino-2,4-dimethoxybenzene; 2,6-bis(2-hydroxyethyl)-aminotoluene; 4-hydroxyindole; 3-dimethylaminophenol; 3-diethylaminophenol; 5-amino-2-methylphenol; 5-amino-4-fluoro-2-methylphenol; 5-amino-4-methoxy-2-methylphenol; 5-amino-4-ethoxy-2-methylphenol; 3-amino-2,4-dichlorophenol; 5-amino-2,4-dichlorophenol; 3-amino-2-methylphenol; 3-amino-2-chloro-6-methylphenol; 3-aminophenol; 2-[(3-hydroxyphenyl)amino]acetamide; 5-[( 2-hydroxyethyl)amino]-4-methoxy-2-methylphenol; 5-[(2-hydroxyethyl)amino]-2-methylphenol; 3-[(2-hydroxyethyl)amino]phenol; 3-[(2-methoxyethyl)amino]phenol; 5-amino-2-ethylphenol; 5-amino-2-methoxyphenol; 2-(4-amino-2-hydroxyphenoxy)ethanol; 5-[(3-hydroxypropyl)amino]-2-methylphenol; 3-[(2,3-dihydroxypropyl)amino]-2-methylphenol; 3-[(2-hydroxyethyl)amino]-2-methylphenol; 2-amino-3-hydroxypyridine; 2,6-dihydroxy-3,4-dimethylpyridine; 5-amino-4-chloro-2-methylphenol; 1-naphthol; 2-methyl-1-naphthol; 1,5-dihydroxynaphthalene; 1,7-dihydroxynaphthalene; 2,3-dihydroxynaphthalene; 2,7-dihydroxynaphthalene; 2-methyl-1-naphthol acetate; 1,3-dihydroxybenzene; 1-chloro-2,4-dihydroxybenzene; 2-chloro-1,3-dihydroxybenzene; 1,2-dichloro-3,5-dihydroxy-4-methylbenzene; 1,5-dichloro-2,4-dihydroxybenzene; 1,3-dihydroxy-2-methylbenzene; 3,4-methylenedioxyphenol; 3,4-methylenedioxyaniline; 5-[(2-hydroxyethyl)amino]-1,3-benzodioxole; 6-bromo-1-hydroxy-3,4-methylenedioxybenzene; 3,4-diaminobenzoic acid; 3,4-dihydro-6-hydroxy-1,4-(2H)benzoxazine; 6-amino-3,4-dihydro-1,4[2H]benzoxazine; 3-methyl-1-phenyl-5-pyrazolone; 5,6-dihydroxyindole; 5,6-dihydroxyindoline; 5-hydroxyindole; 6-hydroxyindole; 7-hydroxyindole and 2,3-indolinedione.

The compounds of formula (I) and the amines and/or phenols are stored separately from each other and are mixed only shortly before use. If the compounds of formula (I) and the amines and/or phenols are solids, however, it is also possible to package them together and to prepare the ready-to-use colorant (A) shortly before use by mixing the compounds of formula (I) and the amines and/or phenols with water or with a liquid preparation containing the other ingredients of the colorant.

In addition to the compounds of formula (I), the amines and phenols in component (A2) and the ready-to-use preparation (A), the colorant of the invention can optionally contain other common, physiologically harmless, direct dyes from the group of nitro dyes, cationic and anionic dyes, disperse dyes, azo dyes, quinone dyes and triphenylmethane dyes.

These direct dyes can be used in component (A2) in a total amount of about 0.02 to 20 wt. %, preferably 0.2 to 10 wt. %, the total amount of direct dyes in the ready-to-use colorant (A) obtained by mixing components (A1) and (A2) being about 0.01 to 10 wt. % and preferably 0.1 to 5 wt. %.

As a rule, the dyeing agent of the invention consists of a mixture of components (A1) and (A2), namely a dye carrier composition (A1) that contains the compound of formula (I) and another dye carrier composition (A2) containing the amines and/or phenols.

Each of the compounds of formula (I) and of the amines and/or phenols are contained in the respective dye carrier composition [component (A1) or component (A2)] in a total amount of about 0.02 to 20 wt. % and preferably about 0.2 to 10 wt. %, in the ready-to-use colorant (A) each of the compounds of formula (I) and of the amines and/or phenols being present in a total amount of about 0.01 to 10 wt. % and preferably about 0.1 to 5 wt. %.

Components (A1) and (A2) and the ready-to-use colorant (A) can be in the form of, for example, a solution, particularly an aqueous or aqueous-alcoholic solution, a cream, a gel or an emulsion. Such a composition consists of a mixture of the compound of formula (I) or of the amines and/or phenols with the usual additives employed for such compositions.

Common colorant additives used in solutions, creams, emulsions, gels or aerosol foams are, for example, solvents such as water, lower aliphatic alcohols, for example, ethanol, n-propanol or isopropanol, or glycols such as glycerol and 1,2-propanediol, moreover wetting agents or emulsifiers from the classes of anionic, cationic, amphoteric or nonionic surface-active agents, for example fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides, ethoxylated fatty alcohols, ethoxylated nonylphenols, fatty acid alkanolamides [sic-Translator] and ethoxylated fatty esters, furthermore thickeners such as the higher fatty alcohols, starch or cellulose derivatives, perfumes, hair-pretreatment agents, conditioners, hair-swelling agents, preservatives, moreover vaselines, paraffin oil and fatty acids, also hair-care agents such as cationic resins, lanolin derivatives, cholesterol, pantothenic acid and betaine. The said constituents are used in amounts commonly employed for such purposes, for example the wetting agents and emulsifiers at a concentration of about 0.5 to 30 wt. % [based on component (A1) or (A2)], the thickeners in an amount from about 0.1 to 25 wt. % [based on component (A1) or (A2)] and the hair-care agents at a concentration from about 0.1 to 5 wt. % [based on component (A1) or (A2)].

The pH of the ready-to-use colorant (A) is about 3 to 12, and preferably about 4 to 10 and as a rule is reached upon mixing component (A1) with component (A2).

To adjust the pH of components (A1) and (A2) and of the ready-to-use colorant (A) to the value desired for dyeing, it is possible—if necessary—to use an alkalinizing agent, for example an alkali metal hydroxide, alkaline earth metal hydroxide, alkali metal acetate, alkaline earth metal acetate, alkali metal carbonate or alkaline earth metal carbonate, or an acid, for example lactic acid, acetic acid, tartaric acid, phosphoric acid, hydrochloric acid, citric acid, ascorbic acid or boric acid.

The ready-to-use colorant is prepared just before application by mixing components (A1) and (A2)—optionally after adding sodium carbonate, sodium hydrogen carbonate or sodium acetate—and is then applied to the fibers, particularly human hair. Depending on the depth of shade desired, this mixture is allowed to act for about 5 to 60 min, preferably about 15 to 30 min, at a temperature of about 20 to 50° C. and particularly about 30 to 40° C. The fibers are then rinsed with water, optionally washed with a shampoo and dried.

Another object of the present invention is a multicomponent kit consisting of an agent of component (A1), an agent of component (A2) and optionally an agent for pH adjustment. Naturally, the agents of components (A1) and (A2) can consist of several individual components which are mixed only just before use. It is also possible to have a 2-component kit in which component 1 consists of a powder containing the compounds of formula (I) and the amines and/or phenols and optionally other common powdered cosmetic additives, and component 2 is water or a liquid cosmetic preparation. Particularly preferred, however, is a 2-component kit consisting of an agent of component (A1) and an agent of component (A2).

The dyeing agent of the invention produces in gentle manner a uniform and durable coloration of the fibers, particularly keratin fibers such as, for example, human hair, permitting a wide range of color shades from yellow to brown-black. Although it is preferred to use the aforesaid agent with-out an oxidant, the aforesaid dyeing agent can readily be used in conjunction with an oxidant, for example when simultaneous bleaching of the fibers is desired or when common oxidation dye precursors are to be added to the dyeing agent.

The compounds of formula (I) can be prepared by known methods, for example in analogy to the methods described in German Unexamined Patent Application DE-12 03 042, in Analen der Chemie 37, (1965), pp. 1395–1399 or in Australian Journal of Chemistry 24 (1971), pp. 1449–1465, by reaction of the appropriate 1,4-benzoquinone-4-oxime of formula (II), which is generally known from the literature or is commercially available, with a sulfonyl chloride or acetic anhydride:

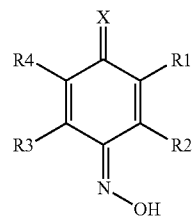

(II)

The 1,4-benzoquinone-4-oximes of formula (II) can be prepared, for example, by a method analogous to those described in the Journal of Organic Chemistry 61 (1996), pp. 2774–2779, or in Tetrahedron 51 (1995), pp. 8447–8458.

The following examples describe the object of the invention in greater detail without limiting its scope.

EXAMPLES

I. Preparation Examples

Example 1

Synthesis of 3-methyl-1,4-benzoquinone-4-[O-(methylsulfonyl)oxime]

A. Synthesis of 3-methyl-1,4-benzoauinone-4-oxime

3-Methyl-1,4-benzoquinone-4-oxime was prepared by reaction of 3-methylphenol with sodium nitrite under basic conditions by the method of T. Ishikawa et al. described in Tetrahedron 31, 1995, page 8454.

B. Synthesis of 2-methyl-1,4-benzoguinone-4-[O-(methylsulfonyl)oxime]

A solution of 1 g (7.28 mmol) of 3-methyl-1,4-benzoquinone-4-oxime in 10 mL of tetrahydrofuran and 0.7 g of triethylamine was cooled to 0° C. To the reaction mixture was then added dropwise 0.92 g (8 mmol) of methyl sulfochloride at 0° C. At the end of the reaction, the reaction mixture was poured onto 150 mL of water/ice. The precipitated product was filtered off, washed with water and then dried.

| Yield: | 1.28 g (82% of the theoretical) | | |
|---|---|---|---|
| Melting point: | 135–136° C. | | |
| Mass spectrum (ESI-MS): | 238 [M + Na]⁺ (100) | | |
| Elemental analysis: | C$_8$H$_9$NO$_4$S (215.23) | | |
| | % C | % H | % N |
| Calcd. | 44.64 | 4.22 | 6.51 |
| Found: | 45.02 | 4.18 | 6.18 |

Example 2

Synthesis of 2-methyl-1,4-benzoquinone-4-[O-(methylsulfonyl)oxime]

A. Synthesis of 2-methyl-1,4-benzoguinone-4-oxime

2-Methyl-1,4-benzoquinone-4-oxime was prepared by reaction of 2-methylphenol with sodium nitrite under acidic conditions by the method described by T. Ishikawa et al. in J. Org. Chem. 1996, 61, page 2778.

B. Synthesis of 2-methyl-1,4-benzoquinone-4-[O-(methylsulfonyl)oxime]

0.7 g (5.1 mmol) of 2-methyl-1,4-benzoquinone-4-oxime was subjected to reaction by a method analogous to that of Example 1B. This gave 0.9 g (85% of the theoretical) of 2-methyl-1,4-benzoquinone-4-[O-(methylsulfonyl)oxime].

| | |
|---|---|
| Melting point: | 100–102° C. |
| Mass spectrum (ESI-MS): | 238 [M + Na]+ (100) |

Example 3

Synthesis of 3-methyl-1,4-benzoquinone-4-[O-(tolylsulfonyl)oxime]

A solution of 1 g (7.28 mmol) of 3-methyl-1,4-benzoquinone-4-oxime in 10 mL of tetrahydrofuran and 0.7 g of triethylamine was cooled to 0° C. To the reaction mixture was then added dropwise 1.52 g (8 mmol) of toluene-4-sulfochloride at 0° C. At the end of the reaction, the reaction mixture was poured onto 200 mL of water/ice. The precipitated product was filtered off, washed with water and dried.

| | | | |
|---|---|---|---|
| Yield: | 1.8 g (85% of the theoretical) | | |
| Melting Point: | 98–100° C. | | |
| Mass spectrum (ESI-MS): | 314 [M + Na]+ (100) | | |
| Elemental analysis: | $C_{14}H_{13}NO_4S$ (291.32) | | |
| | % C | % H | % N |
| Calcd. | 57.72 | 4.50 | 4.81 |
| Found: | 57.54 | 4.58 | 4.44 |

Example 4

Synthesis of 2-methyl-1,4-benzoquinone-4-[O-(tolylsulfonyl)oxime]

1.0 g (7.3 mmol) of 2-methyl-1,4-benzoquinone-4-oxime was subjected to reaction by a method analogous to that of Example 3. This gave 1.87 g (88% of the theoretical) of 2-methyl-1,4-benzoquinone-4-[O-(tolylsulfonyl)oxime].

| | |
|---|---|
| Melting point: | 138–140° C. |
| Mass spectrum (ESI-MS): | 314 [M + Na]+ (100) |

Example 5

Synthesis of 2-chloro-1,4-benzoquinone-4-[O-(tolylsulfonyl)oxime]

A. Synthesis of 2-chloro-1,4-benzoquinone-4-oxime

2-Chloro-1,4-benzoquinone-4-oxime was prepared by reaction of 2-chlorophenol with sodium nitrite under acidic conditions by the method described by T. Ishikawa et al. in J. Org. Chem. 1996, 61, page 2778.

B. Synthesis of 2-chloro-1,4-benzoquinone-4-[O-(tolylsulfonyl)oxime]

0.5 g (3.2 mmol) of 2-chloro-1,4-benzoquinone-4-oxime was subjected to reaction by a method analogous to that of Example 3. This gave 0.8 g (82% of the theoretical) of 2-chloro-1,4-benzoquinone-4-[O-(tolylsulfonyl)oxime].

| | |
|---|---|
| Melting point: | 164–166° C. |
| Mass spectrum (ESI-MS): | 334 [M + Na]+ (100) |

Example 6

Synthesis of 3-methyl-1,4-benzoquinone-4-(O-acetyloxime)

One drop of pyridine was added to a mixture of 0.5 g (3.6 mmol) of 3-methyl-1,4-benzoquinone-4-oxime and 1 mL of acetic anhydride and the resulting mixture was heated to 70° C. At the end of the reaction, the reaction mixture was poured on 10 mL of water/ice. The precipitated product was filtered off, washed with water and then dried.

| | | | |
|---|---|---|---|
| Yield: | 0.32 g (50% of the theoretical) | | |
| Melting point: | 84–87° C. | | |
| Mass spectrum (ESI-MS): | 202 [M + Na]+ (100) | | |
| Elemental analysis: | $C_9H_9NO_3$ (179.18) | | |
| | % C | % H | % N |
| Calcd. | 60.33 | 5.06 | 7.82 |
| Found: | 60.62 | 5.03 | 7.47 |

II. Examples of Colorants

Examples 7 to 28

Hair Colorants

Hair colorant solutions of the following compositions were prepared:

| | Component A(1) |
|---|---|
| 0.00625 mol | of quinonimine derivative of formula (I) as per Table 1 |
| 5.0 g | of ethanol |
| 4.0 g | of decylpolyglucoside (aqueous solution; Plantaren ® 2000, a product of Cognis, Germany) |
| 0.2 g | of disodium ethylenediaminetetraacetate hydrate |
| to 100.0 g | demineralized water |
| | Component (A2) |
| 0.00625 mol | of amine and/or phenol as per Table 1 (in powdered form) |

The aforesaid mixture [component (A1)] was mixed uniformly with the powder containing the amine and/or phenol [component (A2)] after addition of a few drops of saturated sodium hydrogen carbonate solution.

If necessary, the pH was adjusted to the desired value with sodium hydroxide solution or citric acid.

The ready-to-use hair colorant thus obtained was applied to the hair and uniformly spread with a brush. After an exposure time of 30 min at 40° C., the hair was rinsed with luke-warm water and then dried.

The resulting colorations are collected in the following Table 1.

TABLE 1

| Example | Component A1: Compound of Formula (I) | Component A2: Amine or Phenol | Resulting Coloration | Intensity |
|---|---|---|---|---|
| 7 | 3-methyl-1,4-benzoquinone-4-[O-(methylsulfonyl)oxime] | 3-aminophenol | dark-blond | + + |
| 8 | 3-methyl-1,4-benzoquinone-4-[O-(methylsulfonyl)oxime] | 1,3-dihydroxybenzene | ash-blond | + |
| 9 | 3-methyl-1,4-benzoquinone-4-[O-(methylsulfonyl)oxime] | 5-amino-2-methylphenol | red | + + + |
| 10 | 3-methyl-1,4-benzoquinone-4-[O-(methylsulfonyl)oxime] | 2-amino-4-[(2-hydroxyethyl)amino]anisole | violet | + + + |
| 11 | 2-methyl-1,4-benzoquinone-4-[O-(methylsulfonyl)oxime] | 3-aminophenol | dark-blond | + + |
| 12 | 2-methyl-1,4-benzoquinone-4-[O-(methylsulfonyl)oxime] | 1,3-dihydroxybenzene | ash-blond | + |
| 13 | 2-methyl-1,4-benzoquinone-4-[O-(methylsulfonyl)oxime] | 5-amino-2-methylphenol | orange-red | + + + |
| 14 | 2-methyl-1,4-benzoquinone-4-[O-(methylsulfonyl)oxime] | 2-amino-4-[(2-hydroxyethyl)amino]anisole | brown-violet | + + + |
| 15 | 3-methyl-1,4-benzoquinone-4-[O-(tolylsulfonyl)oxime] | 3-aminophenol | blond | + |
| 16 | 3-methyl-1,4-benzoquinone-4-[O-(tolylsulfonyl)oxime] | 1,3-dihydroxybenzene | ash-blond | + |
| 17 | 3-methyl-1,4-benzoquinone-4-[O-(tolylsulfonyl)oxime] | 5-amino-2-methylphenol | red | + + |
| 18 | 3-methyl-1,4-benzoquinone-4-[O-(tolylsulfonyl)oxime] | 2-amino-4-[(2-hydroxyethyl)amino]anisole | violet | + + |
| 19 | 2-methyl-1,4-benzoquinone-4-[O-(tolylsulfonyl)oxime] | 3-aminophenol | dark-blond | + + |
| 20 | 2-methyl-1,4-benzoquinone-4-[O-(tolylsulfonyl)oxime] | 1,3-dihydroxybenzene | ash-blond | + |
| 21 | 2-methyl-1,4-benzoquinone-4-[O-(tolylsulfonyl)oxime] | 5-amino-2-methylphenol | orange-red | + + |
| 22 | 2-methyl-1,4-benzoquinone-4-[O-(tolylsulfonyl)oxime] | 2-amino-4-[(2-hydroxyethyl)aminoanisole | brown-violet | + + |
| 23 | 2-chloro-1,4-benzoquinone-4-[O-(tolylsulfonyl)oxime] | 3-aminophenol | dark-blond | + + |
| 24 | 2-chloro-1,4-benzoquinone-4-[O-(tolylsulfonyl)oxime] | 1,3-dihydroxybenzene | blond | + |
| 25 | 2-chloro-1,4-benzoquinone-4-[O-(tolylsulfonyl)oxime] | 5-amino-2-methylphenol | brown-red | + + |
| 26 | 2-chloro-1,4-benzoquinone-4-[O-(tolylsulfonyl)oxime] | 2-amino-4-[(2-hydroxyethyl)amino]anisole | violet | + + + |
| 27 | 3-methyl-1,4-benzoquinone-4-(O-acetyloxime) | 5-amino-2-methylphenol | yellow | + + |
| 28 | 3-methyl-1,4-benzoquinone-4-(O-acetyloxime) | 2-amino-4-[(2-hydroxyethyl)amino]anisole | brown-violet | + + |

+: low intensity; + +: medium intensity; + + +: high intensity
Unless otherwise indicated, all percentages are by weight.

What is claimed is:

1. An agent for dyeing fibers (A) which is prepared by mixing two components (A1) and (A2), characterized in that component (A1) contains at least one quinonimine derivative of formula (I) and component (A2) contains at least one compound selected from the group consisting of aromatic amines and phenols:

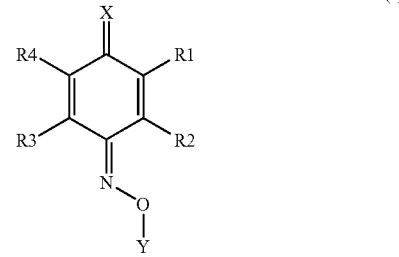
(I)

wherein in formula (I)

X denotes oxygen or an NR group (in which R stands for an optionally substituted $(C_1–C_6)$-alkyl group or an optionally substituted aromatic isocyclic or heterocyclic ring);

Y denotes a $(C_1–C_6)$-alkylsulfonyl group, arylsulfonyl group or acetyl group;

R1, R2, R3 and R4 can be equal or different and independently of each other denote hydrogen, a halogen atom, a $(C_1–C_8)$-alkyl group, a trifluoromethyl group, a halogen-substituted $(C_1–C_6)$-alkyl group, a $(C_1–C_6)$-hydroxyalkyl group, a $(C_2–C_6)$-polyhydroxyalkyl group, a $(C_1–C_6)$-aminoalkyl group, a $(C_1–C_6)$-alkoxy group, a $(C_1–C_6)$-hydroxyalkoxy group, a $(C_1–C_6)$-aminoalkoxy group, a $(C_1–C_6)$-alkoxy-$(C_1–C_6)$-alkyl group, a $(C_1–C_6)$-alkoxy-$(C_1–C_6)$-alkoxy group, a $(C_1–C_6)$-hydroxyalkyl-$(C_1–C_6)$-aminoalkyl group, a nitro group, a cyano group, a carboxyl group, a carboxylate ester group or an optionally substituted aromatic (isocyclic or heterocyclic) ring system, with two adjacent R1 to R4 groups together possibly forming a condensed aromatic (isocyclic or heterocyclic) ring system.

2. The agent according to claim 1, characterized in that in formula (I) X denotes oxygen, Y denotes a methylsulfonyl group, a phenylsulfonyl group, a 4-tolylsulfonyl group, a 4-chlorophenylsulfonyl group, an acetyl group or a chloroacetyl group, and R1, R2, R3 and R4 can be equal or different and independently of each other denote hydrogen, a halogen atom, a $(C_1-C_6)$-alkyl group, a $(C_1-C_6)$-hydroxyalkyl group, a $(C_1-C_6)$-aminoalkyl group, a $(C_1-C_6)$-alkoxy group, a $(C_1-C_6)$-hydroxyalkyl-$(C_1-C_6)$-aminoalkyl group, a $(C_1-C_6)$-alkoxy-$(C_1-C_6)$-alkyl group, a carboxyl group or an optionally substituted aromatic (isocyclic or heterocyclic) ring system with two adjacent R1 to R4 groups together possibly forming a condensed aromatic (isocyclic or heterocyclic) ring.

3. The agent according to claim 1, characterized in that the at least one quinonimine derivative of formula (I) is selected from among the group consisting of
1,4-benzoquinone-4-[O-(methylsulfonyl)oxime];
2-methyl-1,4-benzoquinone-4-[O-(methylsulfonyl)oxime];
2-chloro-1,4-benzoquinone-4-[O-(methylsulfonyl)oxime];
2-bromo-1,4-benzoquinone-4-[O-(methylsulfonyl)oxime];
2-fluoro-1,4-benzoquinone-4-[O-(methylsulfonyl)oxime];
2-hydroxymethyl-1,4-benzoquinone-4-[O-(methylsulfonyl)oxime];
2-hydroxyethyl-1,4-benzoquinone-4-[O-(methylsulfonyl)oxime];
2-aminomethyl-1,4-benzoquinone-4-[O-(methylsulfonyl)oxime];
2-methoxymethyl-1,4-benzoquinone-4-[O-(methylsulfonyl)oxime];
2-[(2-hydroxyethyl)amino]methyl-1,4-benzoquinone-4-[O-(methylsulfonyl)oxime];
2-hydroxycarbonyl-1,4-benzoquinone-4-[O-(methylsulfonyl)oxime];
3-methyl-1,4-benzoquinone-4-[O-(methylsulfonyl)oxime];
3-chloro-1,4-benzoquinone-4-[O-(methylsulfonyl)oxime];
3-bromo-1,4-benzoquinone-4-[O-(methylsulfonyl)oxime];
3-fluoro-1,4-benzoquinone-4-[O-(methylsulfonyl)oxime];
3-hydroxymethyl-1,4-benzoquinone-4-[O-(methylsulfonyl)oxime];
2,6-dichloro-1,4-benzoquinone-4-[O-(methylsulfonyl)oxime];
2,6-dibromo-1,4-benzoquinone-4-[O-(methylsulfonyl)oxime];
2,5-dimethyl-1,4-benzoquinone-4-[O-(methylsulfonyl)oxime];
2-isopropyl-5-methyl-1,4-benzoquinone-4-[O-(methylsulfonyl)oxime];
2-methyl-5-isopropyl-1,4-benzoquinone-4-[O-(methylsulfonyl)oxime];
1,4-naphthoquinone-4-[O-(methylsulfonyl)oxime];
1-phenyliminobenzoquinone-4-[O-(methylsulfonyl)oxime];
1-methyliminobenzoquinone-4-[O-(methylsulfonyl)oxime];
1,4-benzoquinone-4-[O-(phenylsulfonyl)oxime];
2-methyl-4-1,4-benzoquinone-4-[O-(phenylsulfonyl)oxime];
2-chloro-1,4-benzoquinone-4-[O-(phenylsulfonyl)oxime];
2-bromo-1,4-benzoquinone-4-[O-(phenylsulfonyl)oxime];
2-fluoro-1,4-benzoquinone-4-[O-(phenylsulfonyl)oxime];
2-hydroxymethyl-1,4-benzoquinone-4-[O-(phenylsulfonyl)oxime];
2-hydroxyethyl-1,4-benzoquinone-4-[O-(phenylsulfonyl)oxime];
2-aminomethyl-1,4-benzoquinone-4-[O-(phenylsulfonyl)oxime];
2-methoxymethyl-1,4-benzoquinone-4-[O-(phenylsulfonyl)oxime];
2-[(2-hydroxyethyl)amino]methyl-1,4-benzoquinone-4-[O-(phenylsulfonyl)oxime];
2-hydroxycarbonyl-1,4-benzoquinone-4-[O-(phenylsulfonyl)oxime];
3-methyl-1,4-benzoquinone-4-[O-(phenylsulfonyl)oxime];
3-chloro-1,4-benzoquinone-4-[O-(phenylsulfonyl)oxime];
3-bromo-1,4-benzoquinone-4-[O-(phenylsulfonyl)oxime];
3-fluoro-1,4-benzoquinone-4-[O-(phenylsulfonyl)oxime];
3-hydroxymethyl-1,4-benzoquinone-4-[O-(phenylsulfonyl)oxime];
2,6-dichloro-1,4-benzoquinone-4-[O-(phenylsulfonyl)oxime];
2,6-dibromo-1,4-benzoquinone-4-[O-(phenylsulfonyl)oxime];
1,4-benzoquinone-4-[O-4-(tolylsulfonyl)oxime];
2-methyl-1,4-benzoquinone-4-[O-4-(tolylsulfonyl)oxime];
2-chloro-1,4-benzoquinone-4[-O-4-(tolylsulfonyl)oxime];
2-bromo-1,4-benzoquinone-4-[O-4-(tolylsulfonyl)oxime];
2-fluoro-1,4-benzoquinone-4-[O-4-(tolylsulfonyl)oxime];
2-hydroxymethyl-1,4-benzoquinone-4-[O-4-(tolylsulfonyl)oxime];
2-hydroxyethyl-1,4-benzoquinone-4-[O-4-(tolylsulfonyl)oxime];
2-aminomethyl-1,4-benzoquinone-4-[O-4-(tolylsulfonyl)oxime];
2-methoxymethyl-1,4-benzoquinone-4-[O-4-(tolylsulfonyl)oxime];
2-[(2-hydroxyethyl)amino]methyl-1,4-benzoquinone-4-[O-4-(tolylsulfonyl)oxime];
2-hydroxycarbonyl-1,4-benzoquinone-4-[O-4-(tolylsulfonyl)oxime];
3-methyl-1,4-benzoquinone-4-[O-4-(tolylsulfonyl)oxime];
3-chloro-1,4-benzoquinone-4-[O-4-(tolylsulfonyl)oxime];
3-bromo-1,4-benzoquinone-4-[O-4-(tolylsulfonyl)oxime];
3-fluoro-1,4-benzoquinone-4-[O-4-(tolylsulfonyl)oxime];
3-hydroxymethyl-1,4-benzoquinone-4-[O-4-(tolylsulfonyl)oxime];
2,6-dichloro-1,4-benzoquinone-4-[O-4-(tolylsulfonyl)oxime];

2,6-dibromo-1,4-benzoquinone-4-[O-4-(tolylsulfonyl)oxime];
1,4-benzoquinone-4-[O-phenylsulfonyl)oxime];
2-methyl-1,4-benzoquinone-4-[O-4tolylsulfonyl)oxime];
2-chloro-1,4-benzoquinone-4-[O-4tolylsulfonyl)oxime];
2-bromo-1,4-benzoquinone-4-[O-4tolylsulfonyl)oxime];
2-fluoro-1,4-benzoquinone-4-[O-4tolylsulfonyl)oxime];
2-hydroxymethyl-1,4-benzoquinone-4-[O-4tolylsulfonyl)oxime];
2-hydroxyethyl-1,4-benzoquinone-4-[O-4tolylsulfonyl)oxime];
2-aminomethyl-1,4-benzoquinone-4-[O-4tolylsulfonyl)oxime];
2-methoxymethyl-1,4-benzoquinone-4-[O-4tolylsulfonyl)oxime];
2-[(2-hydroxyethyl)amino]methyl-1,4-benzoquinone-4-[O-4tolylsulfonyl)oxime];
2-hydroxycarbonyl-1,4-benzoquinone-4-[O-4tolylsulfonyl)oxime];
3-methyl-1,4-benzoquinone-4-4-[O-4tolylsulfonyl)oxime];
3-chloro-1,4-benzoquinone-4-4-[O-4tolylsulfonyl)oxime];
3-bromo-1,4-benzoquinone-4-4-[O-4tolylsulfonyl)oxime];
3-fluoro-1,4-benzoquinone-4-4-[O-4tolylsulfonyl)oxime];
3-hydroxymethyl-1,4-benzoquinone-4-[O-4tolylsulfonyl)oxime];
2,6-dichloro-1,4-benzoquinone-4-[O-4tolylsulfonyl)oxime];
2,6-dibromo-1,4-benzoquinone-4-[O-4tolylsulfonyl)oxime];
1,4-benzoquinone-4-(O-acetyloxime);
2-methyl-1,4-benzoquinone-4-(O-acetyloxime);
2-chloro-1,4-benzoquinone-4-(O-acetyloxime);
2-chloro-1,4-benzoquinone-4-(O-acetyloxime);
2-bromo-1,4-benzoquinone-4-(O-acetyloxime);
2-fluro-1,4-benzoquinone-4-(O-acetyloxime);
2-hydroxymethyl-1,4-benzoquinone-4-(O-acetyloxime);
2-hydroxyethyl-1,4-benzoquinone-4-(O-acetyloxime);
2-aminomethyl-1,4-benzoquinone-4-(O-acetyloxime);
2-methoxymethyl-1,4-benzoquinone-4-(O-acetyloxime);
2-[(2-hydroxyethyl)amino]methyl-1,4-benzoquinone-4-(O-acetyloxime);
2-hydroxycarbonyl-1,4-benzoquinone-4-(O-acetyloxime);
3-methyl-1,4-benzoquinone-4-(O-acetyloxime);
3-chloro-1,4-benzoquinone-4-(O-acetyloxime);
3-bromo-1,4-benzoquinone-4-(O-acetyloxime);
3-fluoro-1,4-benzoquinone-4-(O-acetyloxime);
3-hydroxymethyl-1,4-benzoquinone-4-(O-acetyloxime);
2,6-dichloro-1,4-benzoquinone-4-(O-acetyloxime) and
2,6-dibromo-1,4-benzoquinone-4-(O-acetyloxime).

4. The agent according to claim 1, characterized in that the at least one quinonimine derivative of formula (I) is selected from the group consisting of
1,4-benzoquinone-4-[O-(methylsulfonyl)oxime];
2-methyl-1,4-benzoquinone-4-[O-(methylsulfonyl)oxime];
2-chloro-1,4-benzoquinone-4-[O-(methylsulfonyl)oxime];
2-bromo-1,4-benzoquinone-4-[O-(methylsulfonyl)oxime];
2-fluoro-1,4-benzoquinone-4-[O-(methylsulfonyl)oxime];
2-hydroxymethyl-1,4-benzoquinone-4-[O-(methylsulfonyl)oxime];
2-hydroxyethyl-1,4-benzoquinone-4-[O-(methylsulfonyl)oxime];
2-aminomethyl-1,4-benzoquinone-4-[O-(methylsulfonyl)oxime];
2-methoxymethyl-1,4-benzoquinone-4-[O-(methylsulfonyl)oxime];
2-[(2-hydroxyethyl)amino]methyl-1,4-benzoquinone-4-[O-(methylsulfonyl)oxime];
2-hydroxycarbonyl-1,4-benzoquinone-4-[O-(methylsulfonyl)oxime];
3-methyl-1,4-benzoquinone-4-[O-(methylsulfonyl)oxime];
3-bromo-1,4-benzoquinone-4-[O-(methylsulfonyl)oxime];
3-fluoro-1,4-benzoquinone-4[O-(methylsulfonyl)oxime];
3-hydroxymethyl-1,4-benzoquinone-4-[O-(methylsulfonyl)oxime];
2,6-dichloro-1,4-benzoquinone-4-[O-(methylsulfonyl)oxime];
2,6-dibromo-1,4-benzoquinone-4-[O-(methylsulfonyl)oxime];
2,5-dimethyl-1,4-benzoquinone-4-[O-(methylsulfonyl)oxime];
2-isopropyl-5-methyl-1,4-benzoquinone-4-[O-(methylsulfonyl)oxime];
2-methyl-5-isopropyl-1,4-benzoquinone-4-[O-(methylsulfonyl)oxime] and 1,4-naphthoquinone-4-[O-(methylsulfonyl)oxime].

5. The agent according to claim 1, characterized in that each of the amines and/or phenols is selected from the group consisting of
N-(3-dimethylaminophenyl)urea; 2,6-diaminopyridine; 2-amino-4-[(2-hydroxyethyl)-amino]anisole; 2,4-diamino-1-fluoro-5-methylbenzene; 2,4-diamino-1-methoxy-5-methylbenzene; 2,4-diamino-1-ethoxy-5-methylbenzene; 2,4-diamino-1-(2-hydroxyethoxy)-5-methylbenzene; 2,4-di[(2-hydroxyethyl)amino]-1,5-dimethoxybenzene; 2,3-diamino-6-methoxypyridine; 3-amino-6-methoxy-2-(methylamino)pyridine; 2,6-diamino-3,5-dimethoxypyridine; 3,5-diamino-2,6-dimethoxypyridine; 1,3-diaminobenzene; 2,4-diamino-1-(2-hydroxyethoxy)benzene; 1,3-diamino-4-(2,3-dihydroxypropoxy)benzene; 1,3-diamino-4-(3-hydroxypropoxy)benzene; 1,3-diamino-4-(2-methoxyethoxy)benzene; 2,4-diamino-1,5-di(2-hydroxyethoxy)benzene; 1-(2-aminoethoxy)-2,4-diaminobenzene; 2-amino-1-(2-hydroxyethoxy)-4-methylaminobenzene; 2,4-diaminophenoxyacetic acid; 3-[di(2-hydroxyethyl)amino]aniline; 4-amino-2-di[(2-hydroxyethyl)amino]-1-ethoxybenzene; phenol; 5-methyl-2-(1-methylethyl)phenol; 3-[(2-hydroxyethyl)amino]aniline; 3-[(2-aminoethyl)amino]aniline; 1,3-di(2,4-diaminophenoxy)propane; di(2,4-diaminophenoxy)methane; 1,3-diamino-2,4-dimethoxybenzene; 2,6-bis(2-hydroxyethyl)aminotoluene; 4-hydroxyindole; 3-dimethylaminophenol; 3-diethylaminophenol; 5-amino-2-methylphenol; 5-amino-4-fluoro-2-methylphenol; 5-amino-4-methoxy-2-methylphenol; 5-amino-4-ethoxy-2-methylphenol; 3-amino-2,4-dichlorophenol; 5-amino-2,4-dichlorophenol; 3-amino-2-methylphenol; 3-amino-2-chloro-6-methylphenol; 3-aminophenol; 2-[(3-hydroxyphenyl)amino]acetamide; 5-[(2-hydroxyethyl)amino]-4-methoxy-2-methylphenol; 5-[(2-hydroxyethyl)amino]-2-methylphenol;

3-[(2-hydroxyethyl)amino]phenol; 3-[(2-methoxyethyl)amino]-phenol; 5-amino-2-ethylphenol; 5-amino-2-methoxyphenol; 2-(4-amino-2-hydroxyphenoxy)ethanol; 5-[(3-hydroxypropyl)amino]-2-methylphenol; 3-[(2,3-dihydroxypropyl)amino]-2-methylphenol; 3-[(2-hydroxyethyl)amino]-2-methylphenol; 2-amino-3-hydroxypyridine; 2,6-dihydroxy-3,4-dimethylpyridine; 5-amino-4-chloro-2-methylphenol; 1-naphthol; 2-methyl-1-naphthol; 1,5-dihydroxynaphthalene; 1,7-dihydroxynaphthalene; 2,3-dihydroxynaphthalene; 2,7-dihydroxynaphthalene; 2-methyl-1-naphthol acetate; 1,3-dihydroxybenzene; 1-chloro-2,4-dihydroxybenzene; 2-chloro-1,3-dihydroxybenzene; 1,2-dichloro-3,5-dihydroxy-4-methylbenzene; 1,5-dichloro-2,4-dihydroxybenzene; 1,3-dihydroxy-2-methylbenzene; 3,4-methylenedioxyphenol; 3,4-methylene-dioxyaniline; 5-[(2-hydroxyethyl)amino]-1,3-benzodioxole; 6-bromo-1-hydroxy-3,4-methylenedioxybenzene; 3,4-diaminobenzoic acid; 3,4-dihydro-6-hydroxy-1,4-[2H]benzoxazine; 6-amino-3,4-dihydro-1,4[2H]benzoxazine; 3-methyl-1-phenyl-5-pyrazolone; 5,6-dihydroxyindole; 5,6-dihydroxyindoline; 5-hydroxyindole; 6-hydroxyindole; 7-hydroxyindole and 2,3-indolinedione.

6. The agent according to claim 1, characterized in that it contains each of the quinonimine derivatives of formula (I) and amines and/or phenols in the respective dye carrier composition [component (A1) or component (A2)] in a total amount of 0.02 to 20 wt. %.

7. The agent according to claim 1, characterized in that it contains each of the quinonimine derivatives of formula (I) and each of the amines and/or phenols in the agent for dyeing fibers (A) in a total amount of 0.01 to 10 wt. %.

8. The agent according to claim 1, characterized in that it contains additionally 0.02 to 20 wt. % of a direct dye selected from the group consisting of cationic and anionic dyes, disperse dyes, nitro dyes, azo dyes, quinone dyes and triphenylmethane dyes.

9. The agent according to claim 1, characterized in that the agent for dyeing fibers (A) has a pH of 3 to 12.

10. The agent according to claim 1, characterized in that it is a hair dyeing agent.

11. A ready-to-use agent for coloring fibers (A), characterized in that it contains at least one quinonimine derivative of formula (I) and at least one compound selected from the group consisting of aromatic amines and phenols and has a pH of 3 to 12:

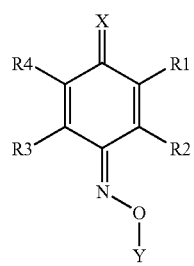

(I)

wherein in formula (I)

X denotes oxygen or an NR group (in which R stands for an optionally substituted ($C_1$–$C_6$)-alkyl group or an optionally substituted aromatic isocyclic or heterocyclic ring);

Y denotes a ($C_1$–$C_6$)-alkylsulfonyl group, arylsulfonyl group or acetyl group;

R1, R2, R3 and R4 can be equal or different and independently of each other denote hydrogen, a halogen atom, a ($C_1$–$C_6$)-alkyl group, a trifluoromethyl group, a halogen-substituted ($C_1$–$C_6$)-alkyl group, a ($C_1$–$C_6$)-hydroxyalkyl group, a ($C_2$–$C_6$)-polyhydroxyalkyl group, a ($C_1$–$C_6$)-aminoalkyl group, a ($C_1$–$C_6$)-alkoxy group, a ($C_1$–$C_6$)-hydroxyalkoxy group, a ($C_1$–$C_6$)-aminoalkoxy group, a ($C_1$–$C_6$)-alkoxy-($C_1$–$C_6$)-alkyl group, a ($C_1$–$C_6$)-alkoxy-($C_1$–$C_6$)-alkoxy group, a ($C_1$–$C_6$)-hydroxyalkyl-($C_1$–$C_6$)-aminoalkyl group, a nitro group, a cyano group, a carboxyl group, a carboxylate ester group or an optionally substituted aromatic (isocyclic or heterocyclic) ring system, with two adjacent R1 to R4 groups together possibly forming a condensed aromatic (isocyclic or heterocyclic) ring system.

12. A method for dyeing keratin fibers, wherein just before use an agent for dyeing fibers (A) is prepared by mixing two components, (A1) and (A2), and is then applied to the hair, and after an exposure time of 5 to 60 min at a temperature of 20 to 50° C. the hair is rinsed with water, optionally washed with a shampoo and then dried, wherein the two components consist of a component (A1) containing at least one quinonimine derivative of formula (I) and a component (A2) containing at least one compound selected from the group consistincvof aromatic amines and phenols:

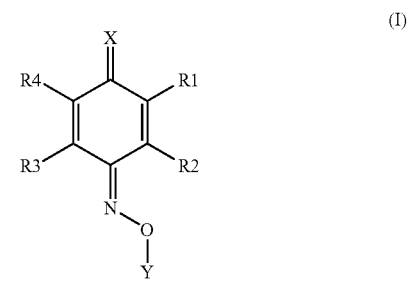

(I)

wherein in formula (I)

X denotes oxygen or an NR group (in which R stands for an optionally substituted ($C_1$–$C_6$)-alkyl group or an optionally substituted aromatic isocyclic or heterocyclic ring);

Y denotes a ($C_1$–$C_6$)-alkylsulfonyl group, arylsulfonyl group or acetyl group;

R1, R2, R3 and R4 can be equal or different and independently of each other denote hydrogen, a halogen atom, a ($C_1$–$C_6$)-alkyl group, a trifluorometh1 group, a halogen-substituted ($C_1$–$C_6$)-alkayl group, a ($C_1$–$C_6$)-hydroxyalkyl group, a ($C_2$–$C_6$)- polyhydro <yalkyl group, a ($C_1$–$C_6$)-aminoalkyl group, a ($C_1$–$C_6$)-alkoxy group, a ($C_1$–$C_6$)-hydroxyalkoxy group, a ($C_1$–$C_6$)-aminoalkyl group, a ($C_1$–$C_6$)-alkoxy group, a ($C_1$–$C_6$)-alkyl group, a ($C_1$–$C_6$)-alkoxy group, a ($C_1$–$C_6$)-hydroxyalkoxy group, a ($C_1$–$C_6$)-aminoalkyl group, a nitro group, a cyano group, a carboxyl group, a carboxylate ester group or an optionally substituted aromatic (isocyclic or heterocyolic) ring system, with two adjacent R1 to R4 groups together possibly forming a condensed aromatic (isocyclic or heterocyclic) ring system.

13. A multi-component kit for dyeing hair, said kit consisting of a component (A1), a component (A2) and optionally an agent for adjusting the pH;

wherein the component (A2) contains at least one compound selected from the group consisting aromatic amines and phenols; and wherein the component (A1) contains at least one quinonimine derivative of formula (I):

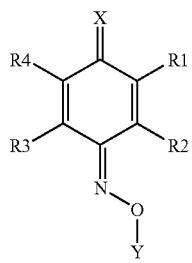

(I)

wherein in formula (I)

X denotes oxygen or an NR group (in which R stands for an otionally substituted $(C_1-C_6)$-alkyl group or an optionally substituted aromatic isocyclic or heterocyclic ring);

Y denotes a $(C_1-C_6)$-alkylsulfonyl group, arylsulfonyl group or acetyl group;

R1, R2, R3 and R4 can be equal or different and independently of each other denote hydrogen, a halogen atom, a $(C_1-C_6)$-alkyl group, a trifluoromethl group, a halogen-substituted $(C_1-C_6)$-alkayl group, a $(C_1-C_6)$-hydroxyalkyl group, a $(C_2-C_6)$- polyhydro <yalkyl group, a $(C_1-C_6)$-aminoalkyl group, a $(C_1-C_6)$-alkoxy group, a $(C_1-C_6)$-hydroxyalkoxy group, a $(C_1-C_6)$-aminoalkyl group, a $(C_1-C_6)$-alkoxy group, a $(C_1-C_6)$-alkyl group, a $(C_1-C_6)$-alkoxy group, a $(C_1-C_6)$-hydroxyalkoxy group, a $(C_1-C_6)$-aminoalkyl group, a nitro group, a cyano group, a carboxyl group, a carboxylate ester group or an optionally substituted aromatic (isocyclic or heterocyolic) ring system, with two adjacent R1 to R4 groups together possibly forming a condensed aromatic (isocyclic or heterocyclic) ring system.

* * * * *